(12) United States Patent
Berner

(10) Patent No.: US 11,109,568 B2
(45) Date of Patent: Sep. 7, 2021

(54) METHOD AND DEVICE FOR ATTACHING AN EAR TAG

(71) Applicant: BERNER INNOVATIONS GMBH, Fürth (DE)

(72) Inventor: Alexander Berner, Fürth (DE)

(73) Assignee: Berner Innovations GmbH, Fürth (DE)

( * ) Notice: Subject to any disclaimer, the term of this patent is extended or adjusted under 35 U.S.C. 154(b) by 307 days.

(21) Appl. No.: 16/193,915

(22) Filed: Nov. 16, 2018

(65) Prior Publication Data

US 2019/0082652 A1    Mar. 21, 2019

Related U.S. Application Data

(63) Continuation of application No. 14/903,187, filed as application No. PCT/EP2014/002022 on Jul. 24, 2014, now abandoned.

(30) Foreign Application Priority Data

Jul. 30, 2013    (DE) .................... 10 2013 012 554.5

(51) Int. Cl.
*A01K 11/00*    (2006.01)
*A61B 10/02*    (2006.01)
*G01N 1/08*    (2006.01)

(52) U.S. Cl.
CPC .......... *A01K 11/002* (2013.01); *A01K 11/003* (2013.01); *A61B 10/0266* (2013.01); *G01N 2001/085* (2013.01)

(58) Field of Classification Search
CPC ..... A01K 11/00–004; G01N 2001/065; G01N 2001/066; G01N 2001/085; A61B 10/0096; A61B 10/02; A61B 10/0208; A61B 10/0233; A61B 10/0266; A61B 10/0275; A61B 10/06; A61B 2010/0208
See application file for complete search history.

(56) References Cited

U.S. PATENT DOCUMENTS

| | | | |
|---|---|---|---|
| 4,597,208 A | 7/1986 | Chevillot et al. | |
| 7,441,354 B2* | 10/2008 | Ritchey | A01K 11/003 119/655 |
| 8,486,088 B2 | 7/2013 | Ritchey et al. | |

(Continued)

FOREIGN PATENT DOCUMENTS

| WO | WO-2006000869 | 1/2006 |
|---|---|---|
| WO | WO-2007013820 | 2/2007 |

OTHER PUBLICATIONS

PCT/EP2014/002022, Search Report and Written Opinion, dated Oct. 14, 2014, 1-8.

*Primary Examiner* — David J. McCrosky
(74) *Attorney, Agent, or Firm* — Rankin, Hill & Clark LLP

(57) ABSTRACT

To attach an ear tag (6, 10) to an ear (16) and to remove a sample (22) containing tissue of the ear therefrom, a mandrel (8), which is fastened to a mandrel region (6) of the ear tag, is brought by means of pliers (1) on a first movement path through the ear (16) into a hole (12) formed in a hole part (10) of the ear tag and anchored there, while the sample (22) is taken with the aid of a removal head (17) and is brought out of engagement with the hole (12) by interaction with the mandrel (8) with a movement component oriented transversely to the first movement path, before the mandrel (8) is anchored in said hole.

19 Claims, 19 Drawing Sheets

(56) References Cited

U.S. PATENT DOCUMENTS

Figure 1A:
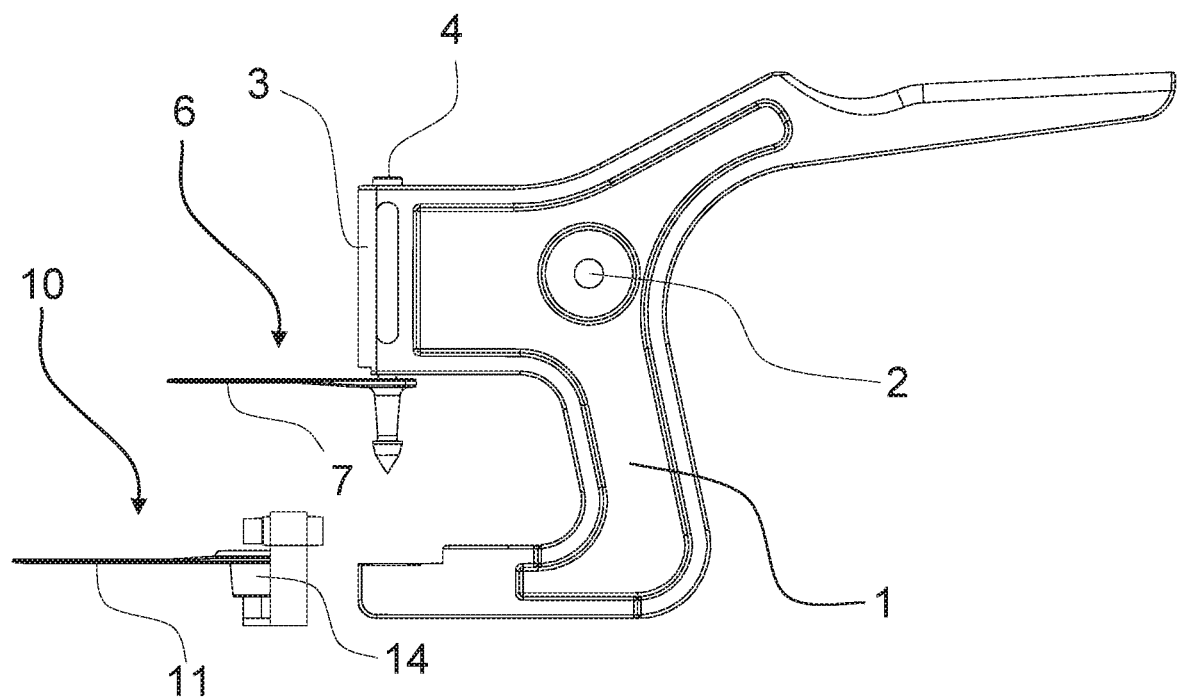

| | | |
|---|---|---|
| 8,622,929 B2 | 1/2014 | Wilson et al. |
| 2010/0210011 A1 | 8/2010 | Hilpert et al. |
| 2016/0249586 A1 | 9/2016 | Berner |

* cited by examiner

METHOD AND DEVICE FOR ATTACHING AN EAR TAG

RELATED APPLICATIONS

This application is a continuation of U.S. application Ser. No. 14/903,187 filed Jan. 6, 2016, which is a U.S. National Stage application under § 371 of PCT/EP2014/002022 filed Jul. 24, 2014, which claims priority to DE102013012554.5 filed Jul. 30, 2013, both of which are incorporated herein by reference in their entireties.

DESCRIPTION

The invention relates to a method for attaching an ear tag and to a device.

Ear tags for identifying farm animals have become established worldwide. Only very few cows, goats or sheep which are not fitted with ear tags are still to be found. These ear tags are used primarily for identification for the purpose of organizing and recording livestock, association with the owners and the traceability of farm animals.

An indispensable part of this is safeguarding against attempts to defraud. In particular, an ear tag must be prevented from being removed from an animal and transferred to another.

A two-part ear tag is shown in U.S. Pat. No. 4,597,208A. A hole plate with a hole and a mandrel plate with a mandrel are connected by stamping the mandrel through the ear and inserting it into the hole where it is locked by means of an undercut. To protect against tampering, the hole is covered on the outside by a stable cap, which prevents attempts at tampering or draws attention to such attempts by obvious signs of damage.

Extensive laboratory investigations of farm animals have been carried out, particularly for combating animal diseases and for gene analysis for breeding purposes. To simplify the work here, it is recommended that the removal of a tissue sample from the animal be associated with the identification. A suitable ear tag for this purpose is shown in the generic US 2010/0210011 A1. This ear tag basically corresponds to the design of the known design previously described, but additionally has a removable head, which is fixed in front of the mandrel in the insertion direction thereof and, when the ear is pierced, removes a sample therefrom by means of a front ring cutter. A disadvantage with this, however, is that, after the mandrel has engaged in the hole, the removal head is pushed through the hole and is arranged exposed behind it. Covering the back of the hole in order to prevent tampering, as the publication mentioned in the introduction shows, is not possible in this case, as the back of the hole must remain freely accessible in order to be able to remove the sample from there.

For these reasons, the known generic prior art has considerable security shortcomings. For example, it is relatively easily possible to press on the mandrel from the back of the hole and push it back through the hole and then use it again.

The object of the present invention therefore consists in increasing protection against tampering for a generic device.

According to the invention, with the generic device, the removal head and the mandrel are designed to work together in such a way that the action thereof on the sample results in a movement path which has a transversely oriented movement component at least in one region. This results in a movement of the sample which removes it sideways from the movement path of the mandrel. This prevents the mandrel taking the sample with it through the hole. With a substantially conventional device, the mandrel can be anchored in the hole, which can be designed to prevent tampering in any way, e.g. fitted with a protective cap on the rear. However, this does not prevent the sample from being removed, as, because of its transversely oriented movement component, it does not move into the protective cap but is conveyed to a different place where it remains easily accessible.

All conventional techniques for preventing tampering, such as protective caps for the hole, for example, can therefore be used here. According to the invention, long-established and officially approved ear tag designs, which enable a sample to be removed while maintaining a high level of tampering protection, can be used.

The severing action may be integrated into the device according to the invention particularly easily, e.g. in the manner of cutting shears, wherein, advantageously, the transverse component can also be produced in an uncomplicated manner by utilizing the movement of the cutting members.

Advantageously, the cutting members can be formed by the mandrel and a container, which for example can be the container for dispatching the sample and can also be formed by the removal head. This enables the design to be greatly simplified while avoiding additional parts. The possibility even exists of using the hole of the hole part as a fixed cutting member.

Advantageously, the mandrel has an angled surface, which can be used to good effect in the cutting process and is also suitable for producing the transverse movement.

At the same time, advantageously, the surface is designed as a conical surface. As a result, an angled surface, which is symmetrical all round, is provided. The ability to use conventional ear tags with a conical mandrel is also advantageous here.

With the severing collision between mandrel and removal head, a cutter can facilitate severing by means of a cutting effect.

Alternatively or in addition, a needle arrangement can facilitate severing. This can fix the ear on the removal head in the region of the sample so that severing by tearing occurs during the relative movement with respect to the mandrel. This also prevents the ear from being pushed aside without obtaining a sample. The needle arrangement does not necessarily have to have actual needles. It can also consist merely of a rough surface region which holds the sample securely when sufficient force is applied.

Advantageously, the removal head has a slot, which can also be designed as a predetermined breaking point and which is designed such that, after the mandrel has passed through, it allows the mandrel shaft to pass easily and without damage on its subsequent sideways removal movement.

An alternative design arises, according to which the removal head is arranged in the conventional manner in front of the mandrel and is therefore moved thereby towards the hole. However, the deflecting device in the region of the hole part ensures that the removal head with the sample lying therein is deflected to the side before reaching the hole part.

A further alternative embodiment arises. Here, the removal head runs on a second movement path which crosses the first movement path at the point of penetration of the ear.

Figure 2A:
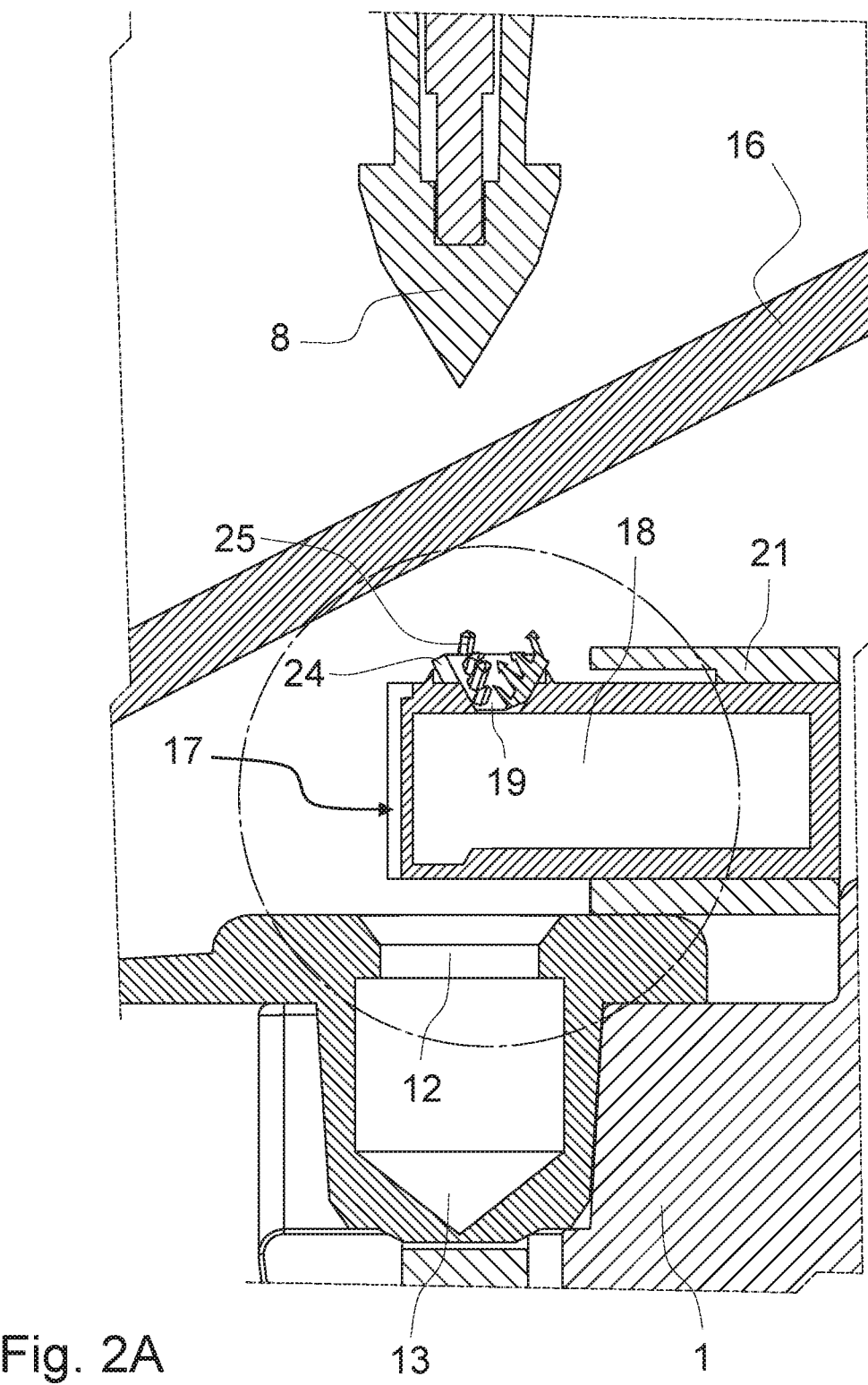
Figure 2B:
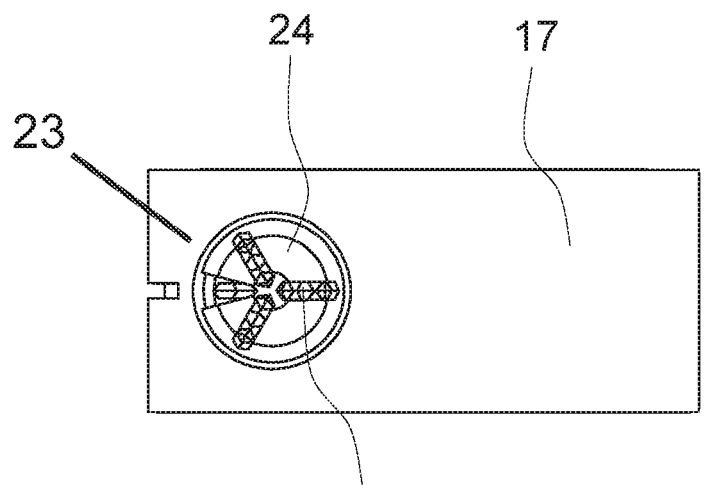
Figure 2C:
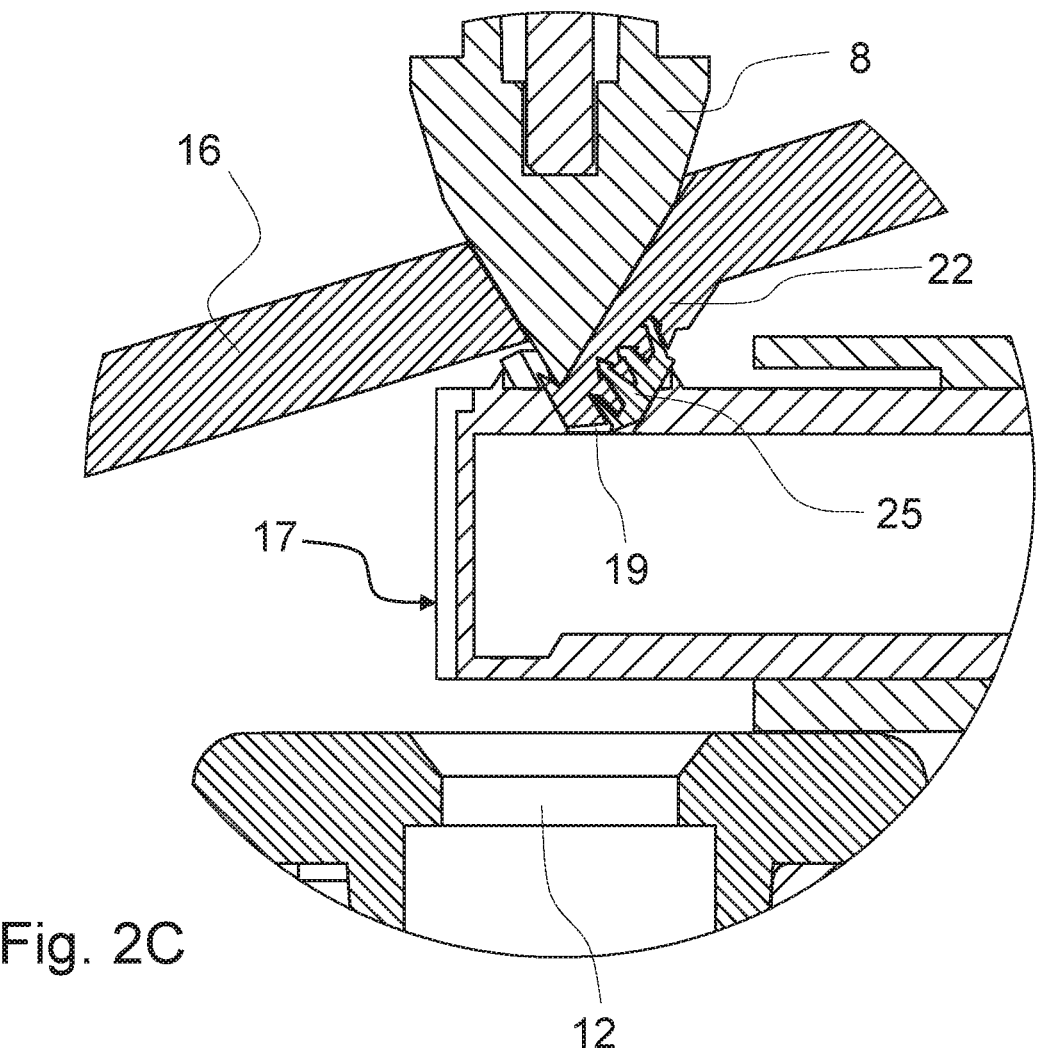
Figure 2D:
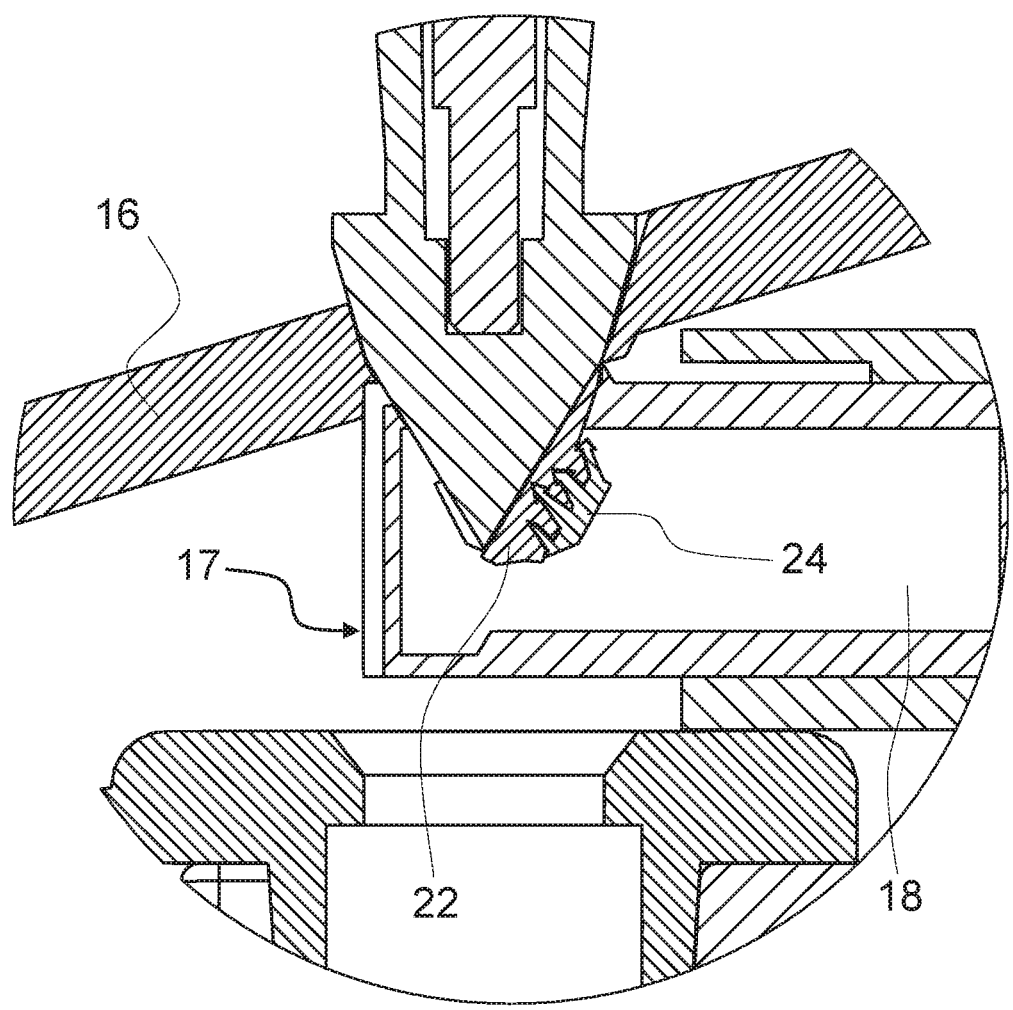
Figure 2E:
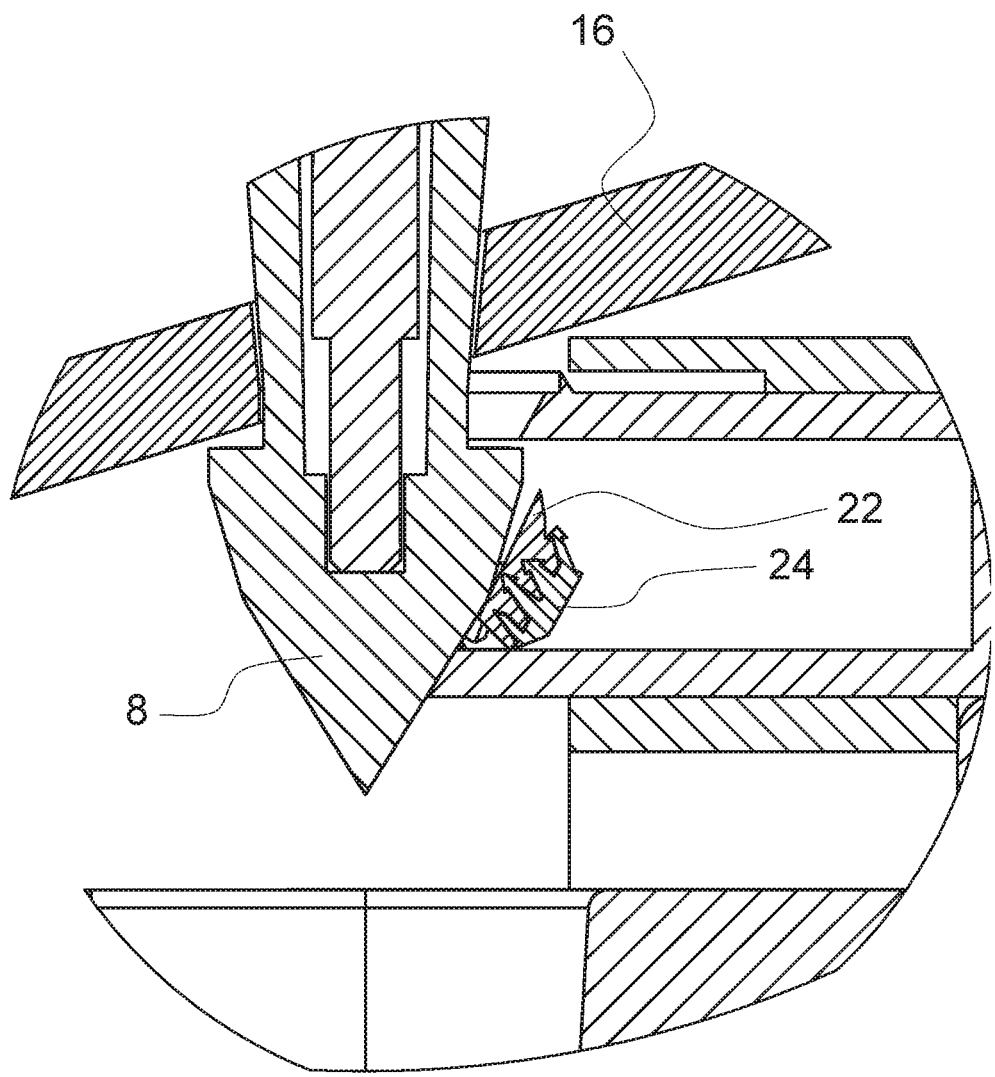
Figure 2F:
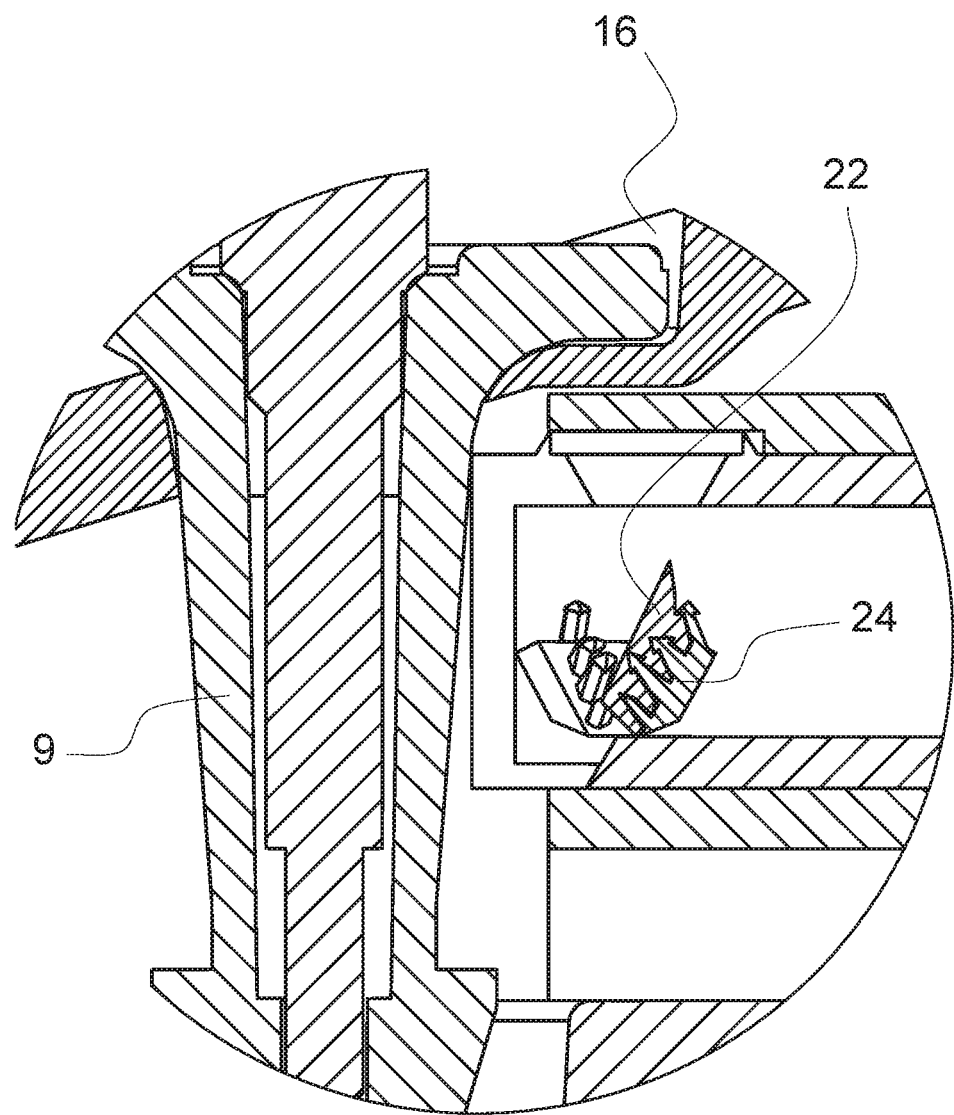
Figure 3A:
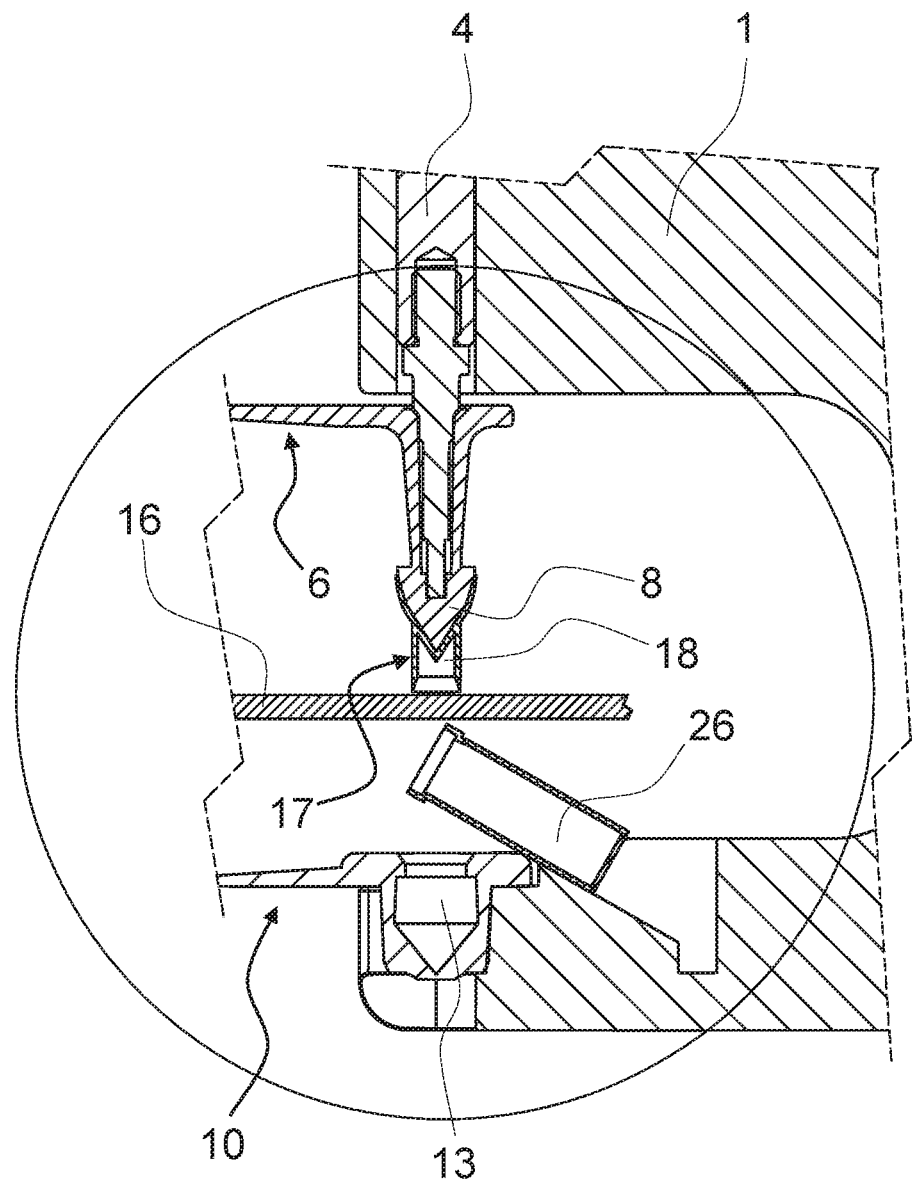
Figure 3B:
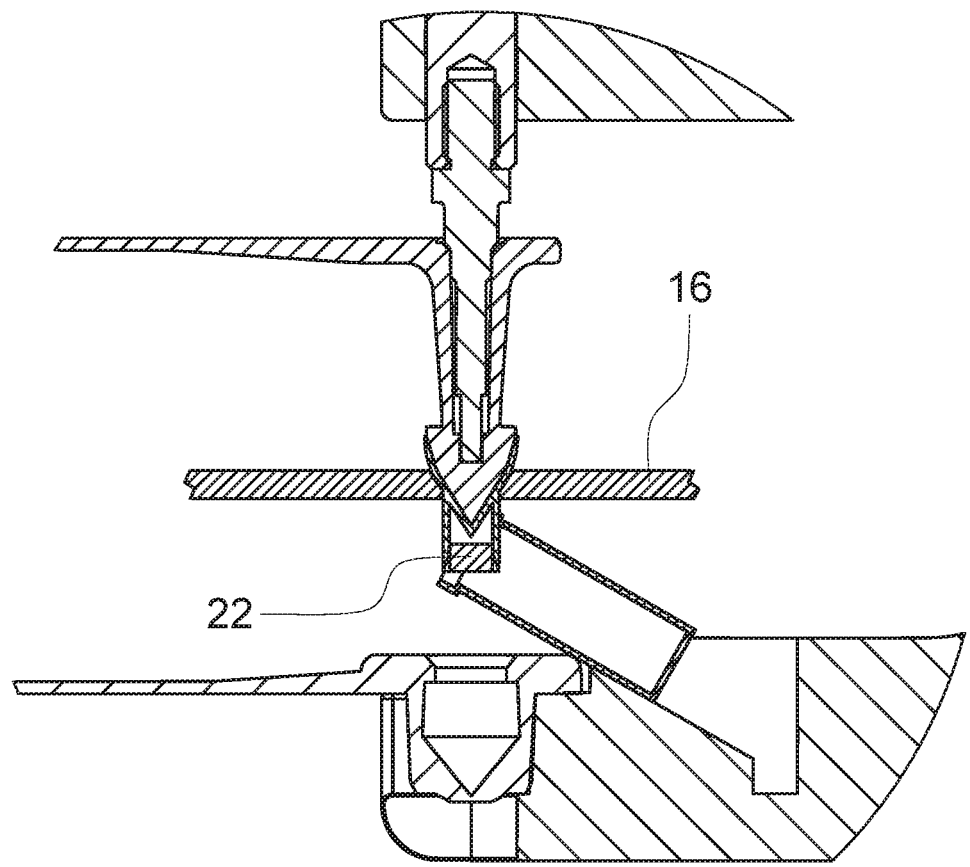
Figure 3C:
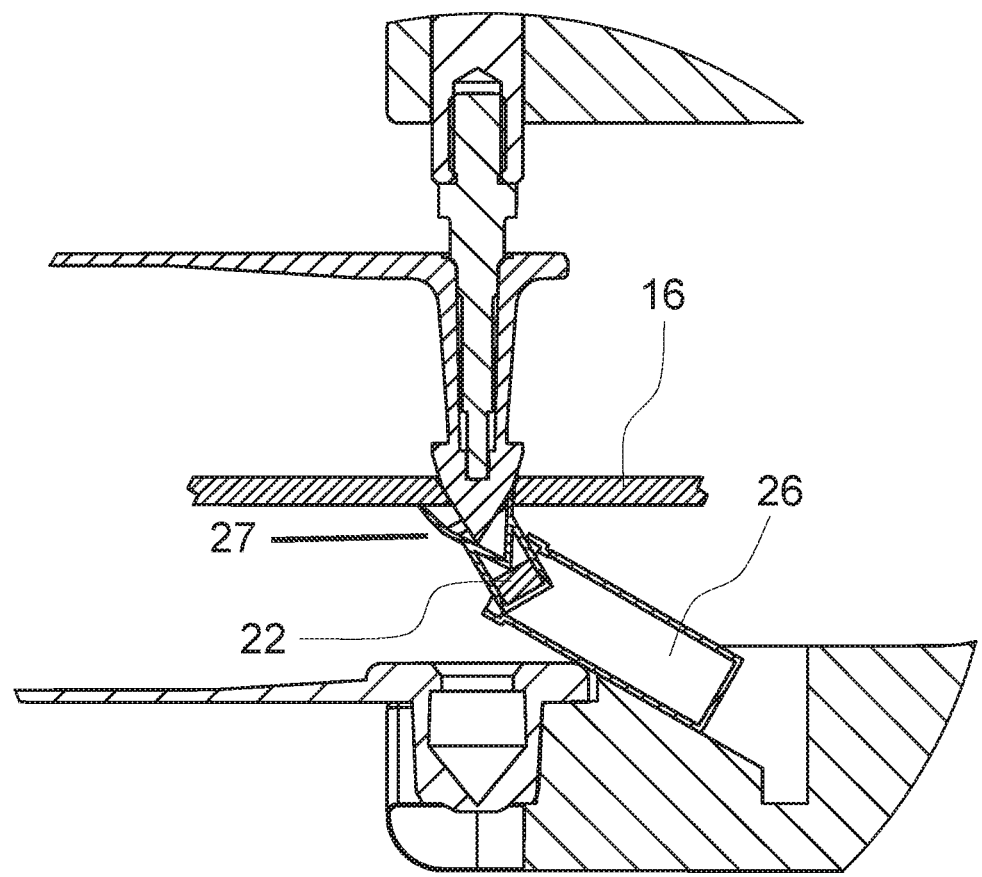
Figure 3D:
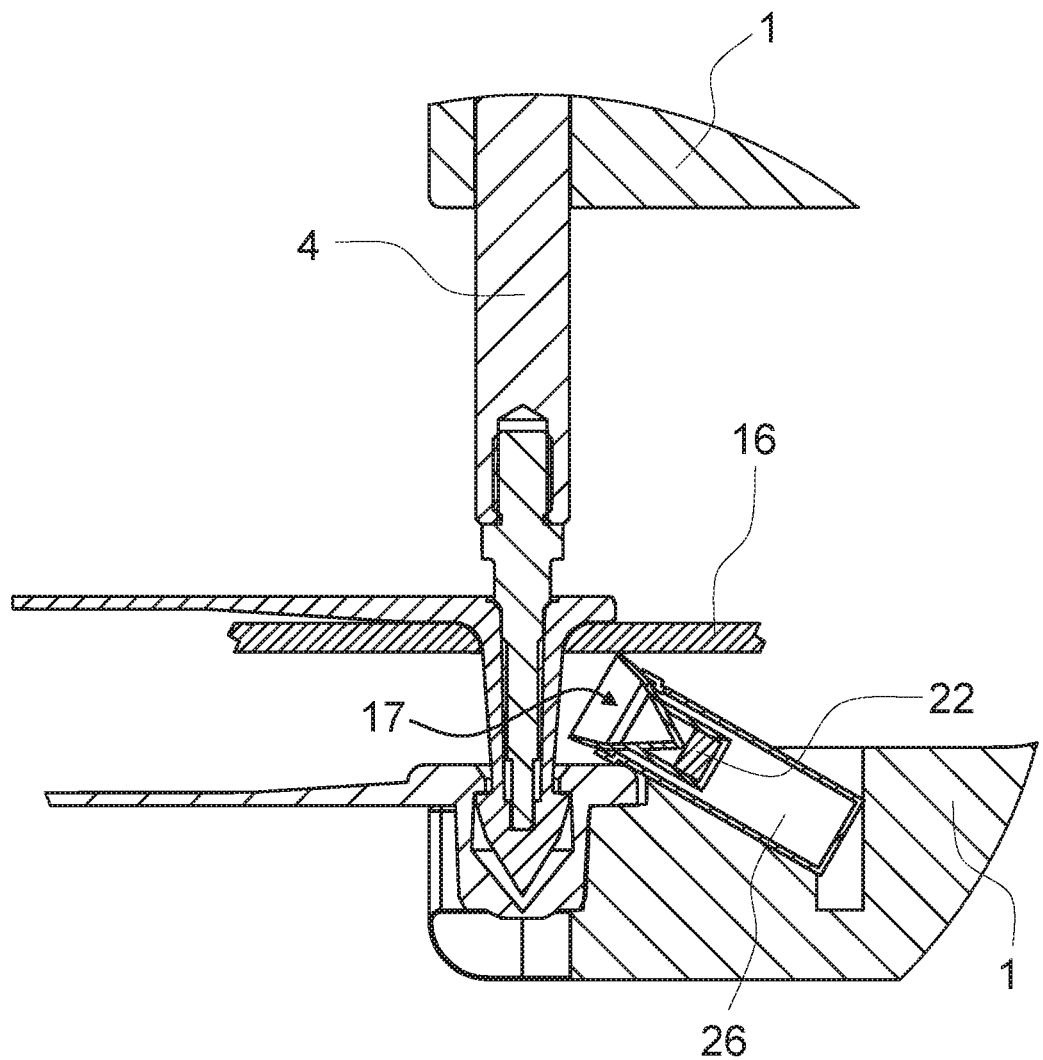
Figure 4A:
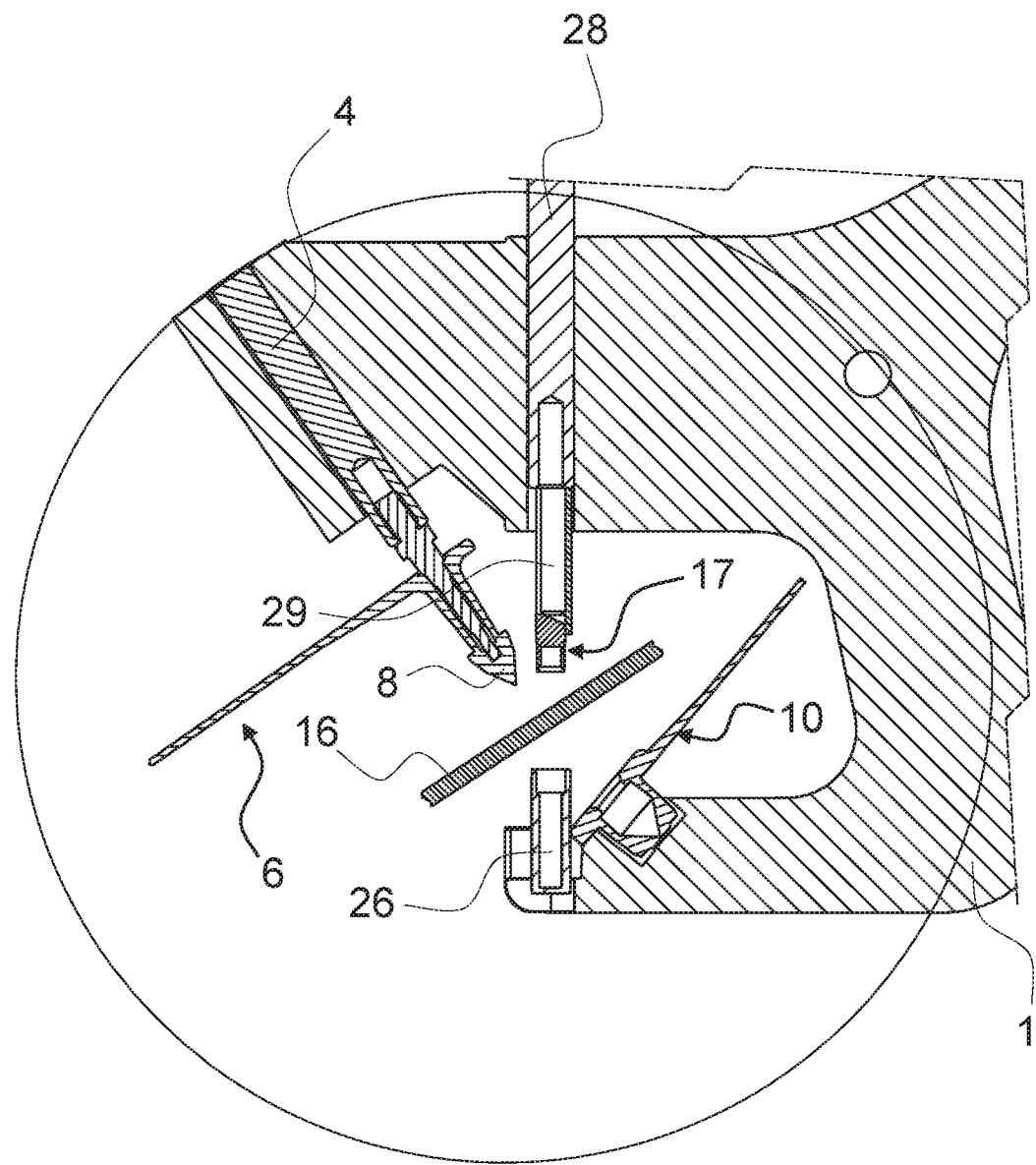
Figure 4B:
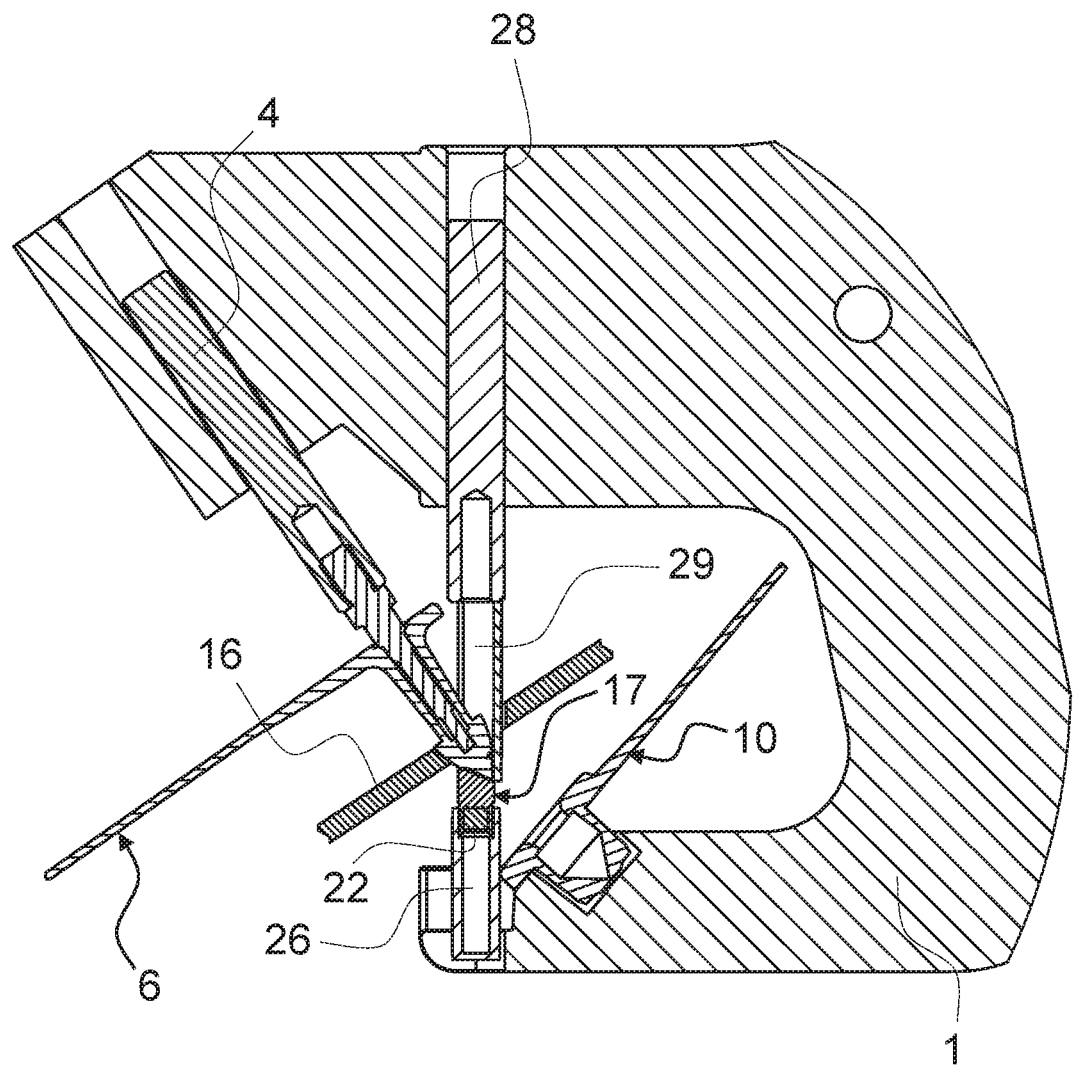
Figure 4C:
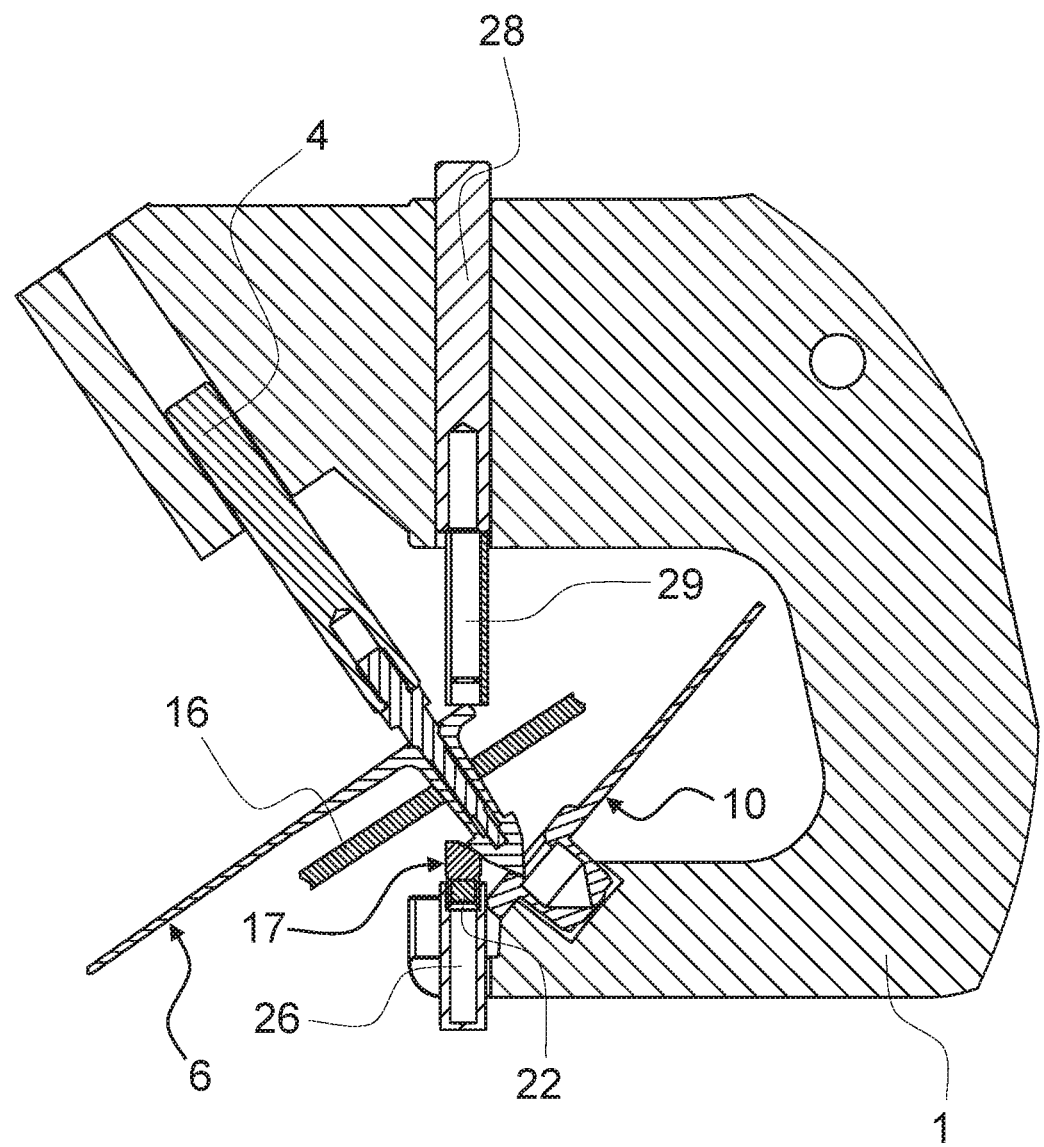

The invention is shown by way of example and schematically in the drawings. In the drawings:

FIGS. 1A-1G show different phases of the relative movement between mandrel and removal head in a first embodiment of the invention, FIGS. 2A-2F show different phases of the relative movement between mandrel and removal head in a second embodiment of the invention, FIGS. 3A-3D show different phases of the relative movement between mandrel and removal head in a third embodiment of the invention, and FIGS. 4A-4C show different phases of the relative movement between mandrel and removal head in a fourth embodiment of the invention.

Figure 1B:
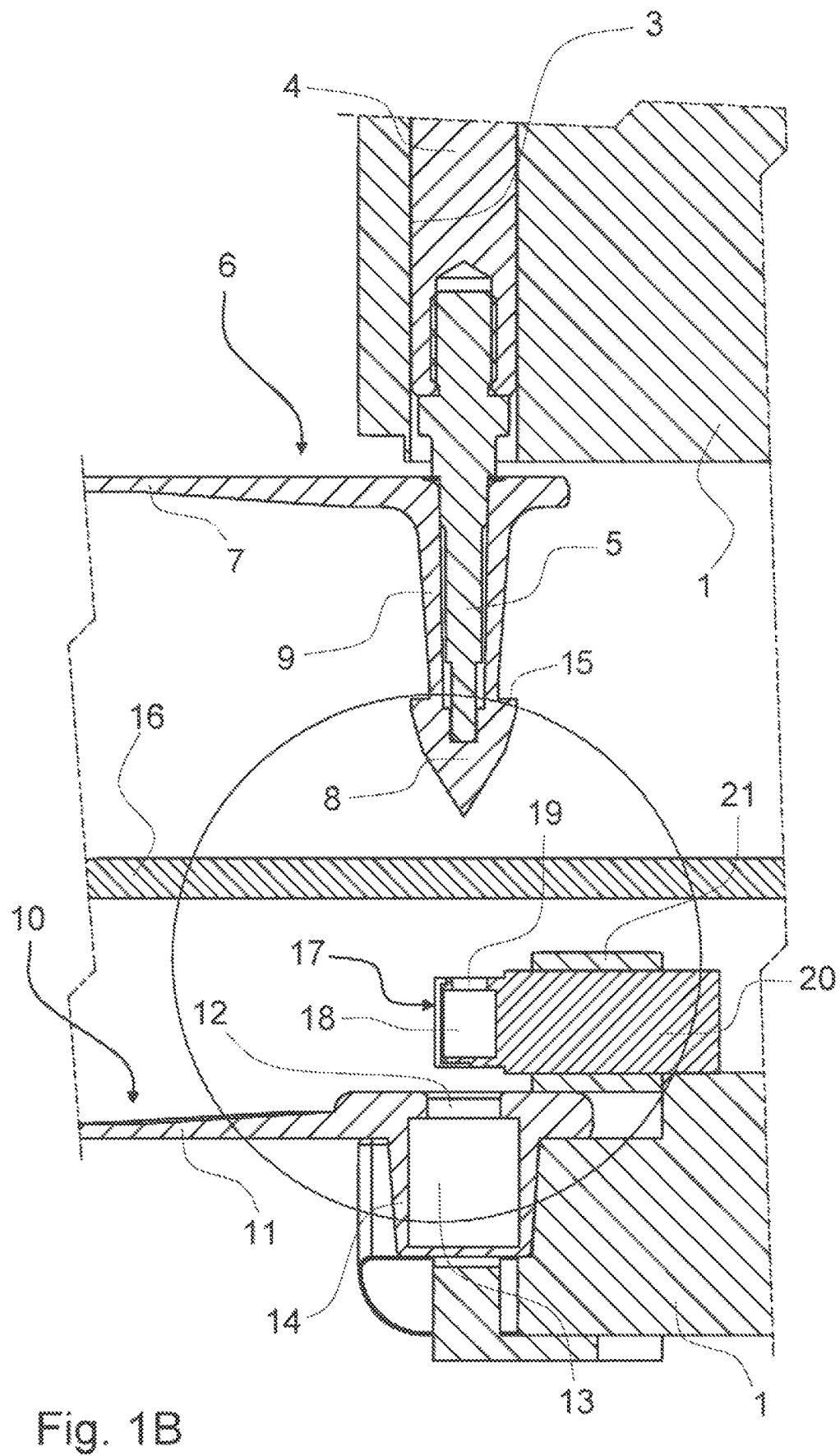

FIGS. 1A-1G show a first embodiment of the invention, wherein a side view of the complete device with applicator pliers 1 is shown in FIG. 1A. These applicator pliers consist of two parts which are mounted so that they can pivot against one another about an axis hole 2, one of which has been omitted in order to simplify the drawing. In the part of the applicator pliers 1 shown, a bolt 4, which, as FIG. 1B shows, carries a mandrel pin 5 at its bottom end, is movably mounted in a guide hole 3. The bolt 4 is connected in a manner (not shown) by means of appropriate kinematics to the second part of the applicator pliers 1 (not shown) and is driven by plier-like pivoting of the two parts of the applicator pliers.

As FIG. 1B shows, a mandrel part 6 of an ear tag is fitted on the mandrel pin 5 shown in FIG. 2. The mandrel part 6 has a mandrel plate 7, to which a conically shaped mandrel 8 is connected by means of a mandrel shaft 9. The mandrel shaft is hollow to accommodate the mandrel pin 1, as FIG. 1B shows.

A hole part 10 forms the second part of the ear tag. It has a hole plate 11 in which, as FIG. 1B shows, a hole 12 is arranged. On the side of the hole 12 opposite the mandrel 8, said hole is sealed in a tamperproof manner by a housing 14 which encompasses a chamber 13. The chamber 13 widens relative to the diameter of the hole 12, so that, after penetrating the hole 12, the mandrel 8 can engage with its edge 15 behind the edge of the hole 12. The parts 6, 10 of the ear tag are thereby secured to one another. Access to the mandrel 8 for the purpose of tampering is prevented by the wall 14 of the chamber 13.

An ear 16, for example the ear of a cow to which the ear tag 6, 7 is to be fixed, is also shown in FIG. 1B. In doing so, a tissue sample is also to be removed. This is shown with reference to the subject matter of FIG. 1B in successive movement phases, which are shown in FIGS. 1B to 1G.

A removal head 17 is arranged underneath the ear 16 in the vicinity of the hole 12, as can be seen in FIG. 1B. The removal head 17 forms a removal chamber 18, which is closed all around and has a removal opening 19 on the top side facing the mandrel 8. The removal head 17 is mounted on the applicator pliers 1 by means of a plunger 20 in a tubular guide 21 so that it can move in a direction perpendicular to the axis of the mandrel 8.

At the beginning of the process for handling an ear, the ear tag parts 6 and 10 are first attached to the applicator pliers 1, as FIG. 1B shows. At the same time, the removal head 17 is also fitted in the manner shown in FIG. 1B. In the position according to FIG. 1B, the mandrel 8 is at the very top. The ear is arranged under the mandrel 8. The mandrel 8 is now driven downwards by actuating the applicator pliers. As FIG. 1O shows, it first pushes the ear 16 downwards as far as the removal head 17 and, in doing so, cuts into the ear 16 as FIG. 1O shows. At the same time, due to the shape of the opening 19 of the removal head 17 and that of the mandrel 8, as shown in FIG. 10, a sample 22 is severed from the tissue of the ear 16 and, as FIG. 1D shows, deposited in the removal chamber 18.

Here, as one cutting member, the conical surface of the mandrel 8 cuts against the top edge of the opening 19 as the second cutting member, as a result of which the sample 22 is severed from the ear 16. This severing action may be incomplete and leave a connecting strand between the sample 22 and the ear 16. This can then be torn or cut in a final severing action. For this purpose, for example, a second, step-shaped edge arranged below the top edge can be provided on the opening 19.

Figure 1C:
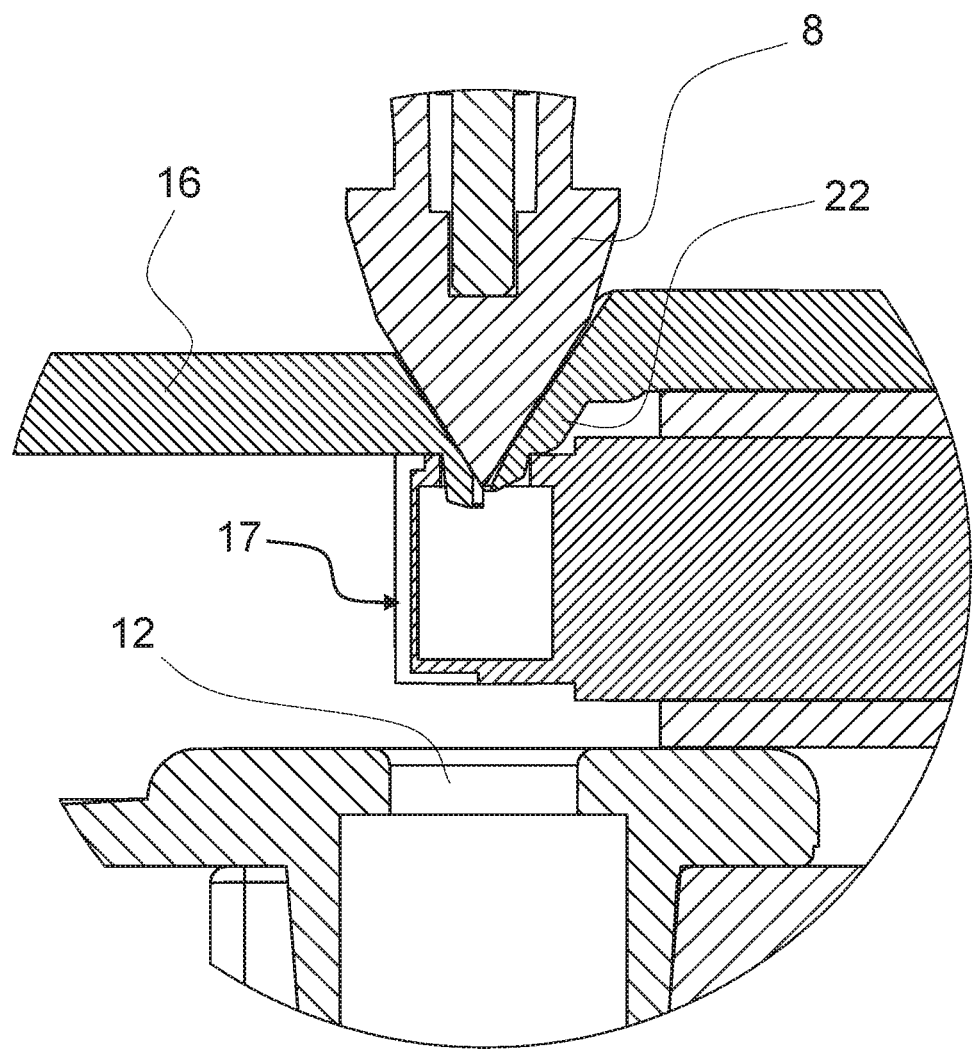
Figure 1D:
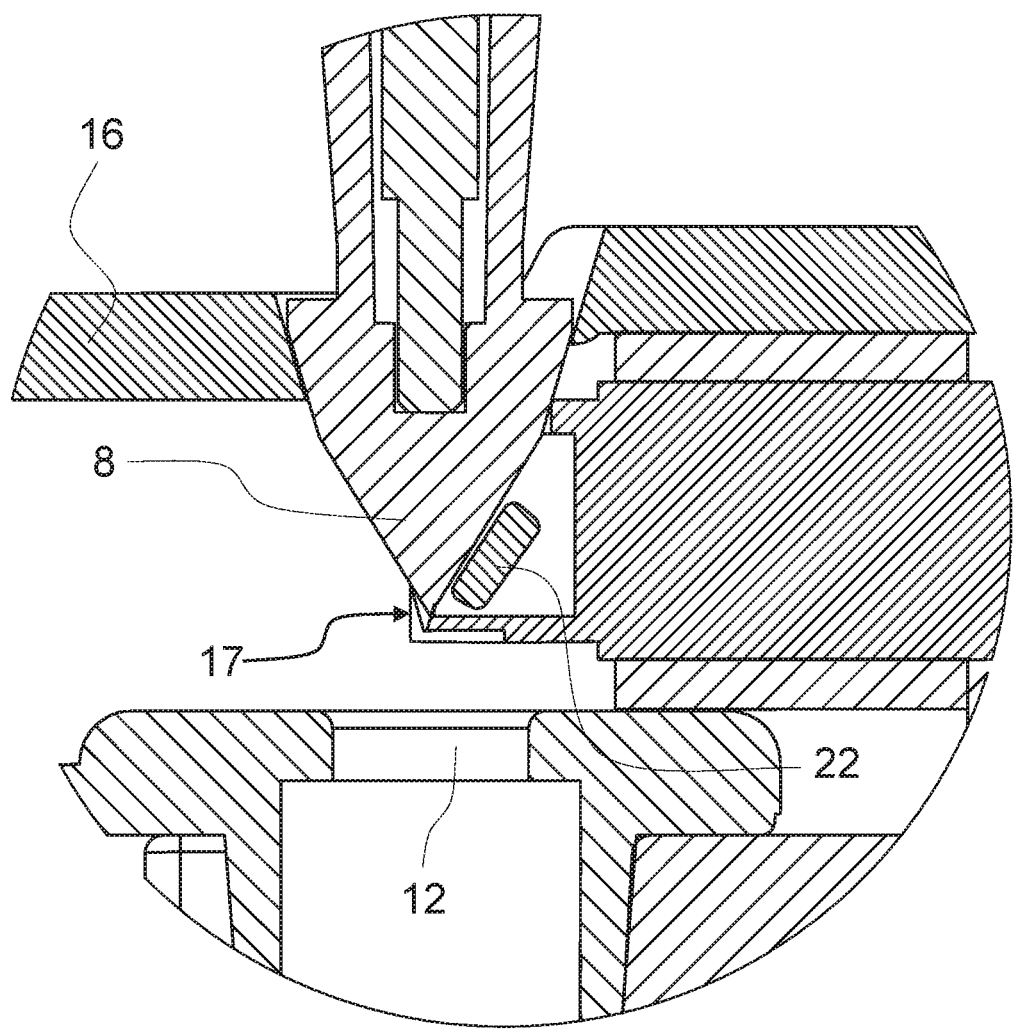
Figure 1E:
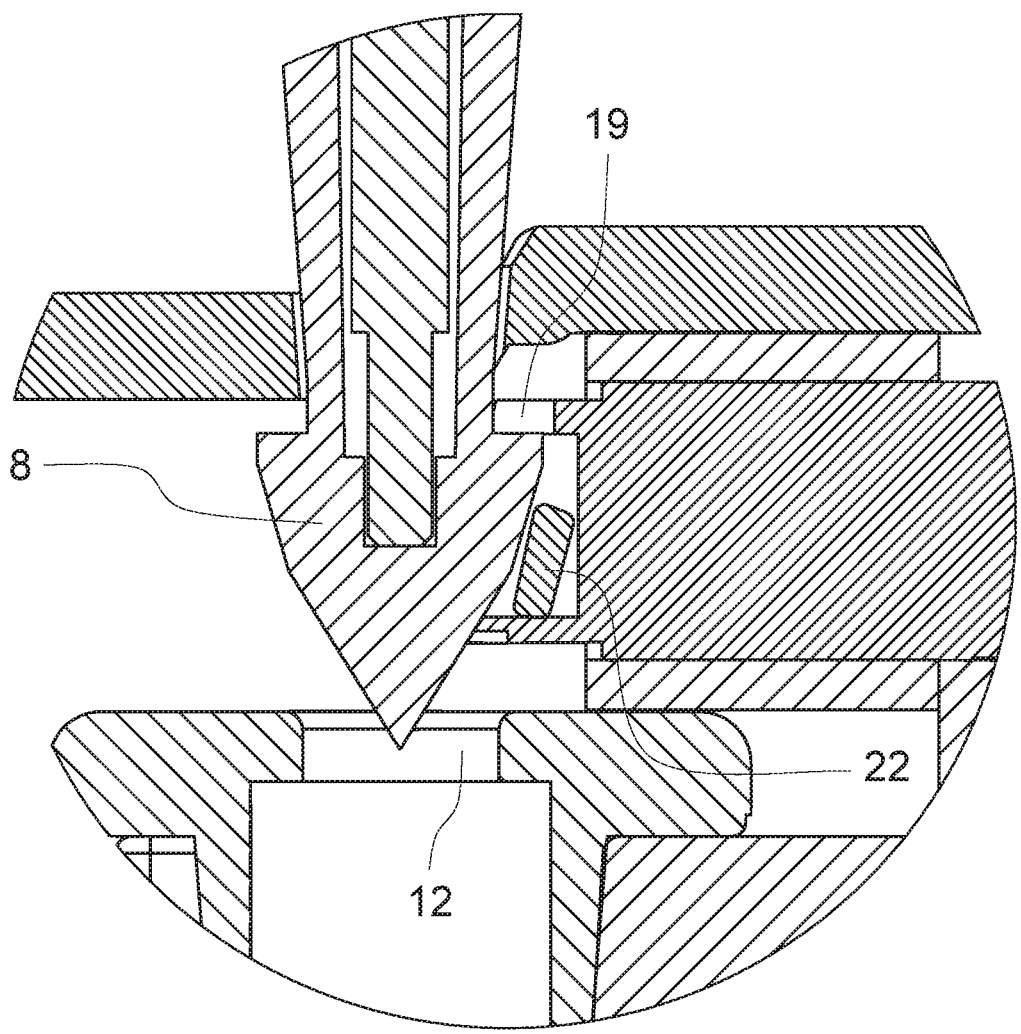

FIG. 1E shows that, when lowered further, the mandrel 8 passes down through the removal head 17 from above and penetrates the hole 12. In the next movement step according to FIG. 1F, the mandrel 8 has reached the bottom point of its movement. It now sits in the chamber 13 engaged behind the edge of the hole 12. The sample 22 lies unimpeded next to the mandrel shaft 9 in the removal chamber 18.

Figure 1F:
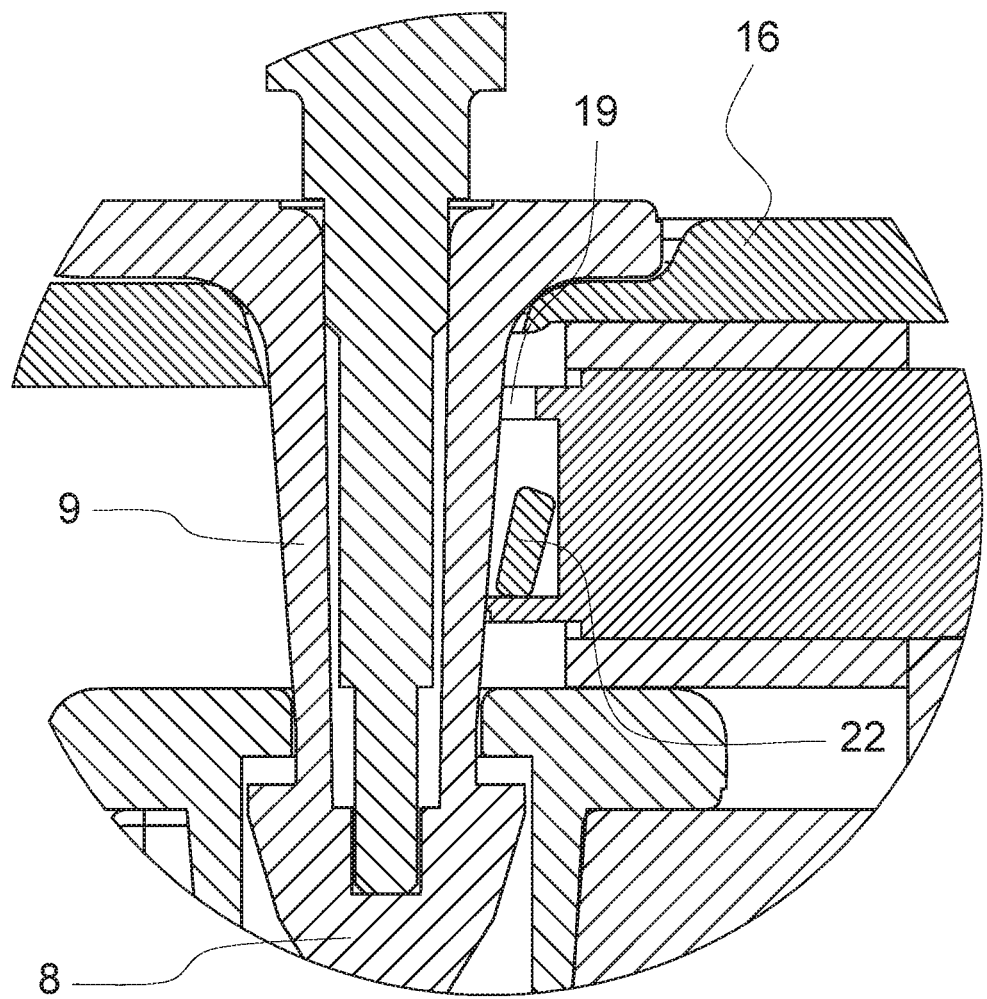

In the position of FIG. 1F, the attachment process of the ear tag is completed by the secure locking of these two ear tag parts according to FIG. 1F, and likewise the removal process of the sample 22, which now lies in its target location in the removal chamber 18.

Figure 1G:
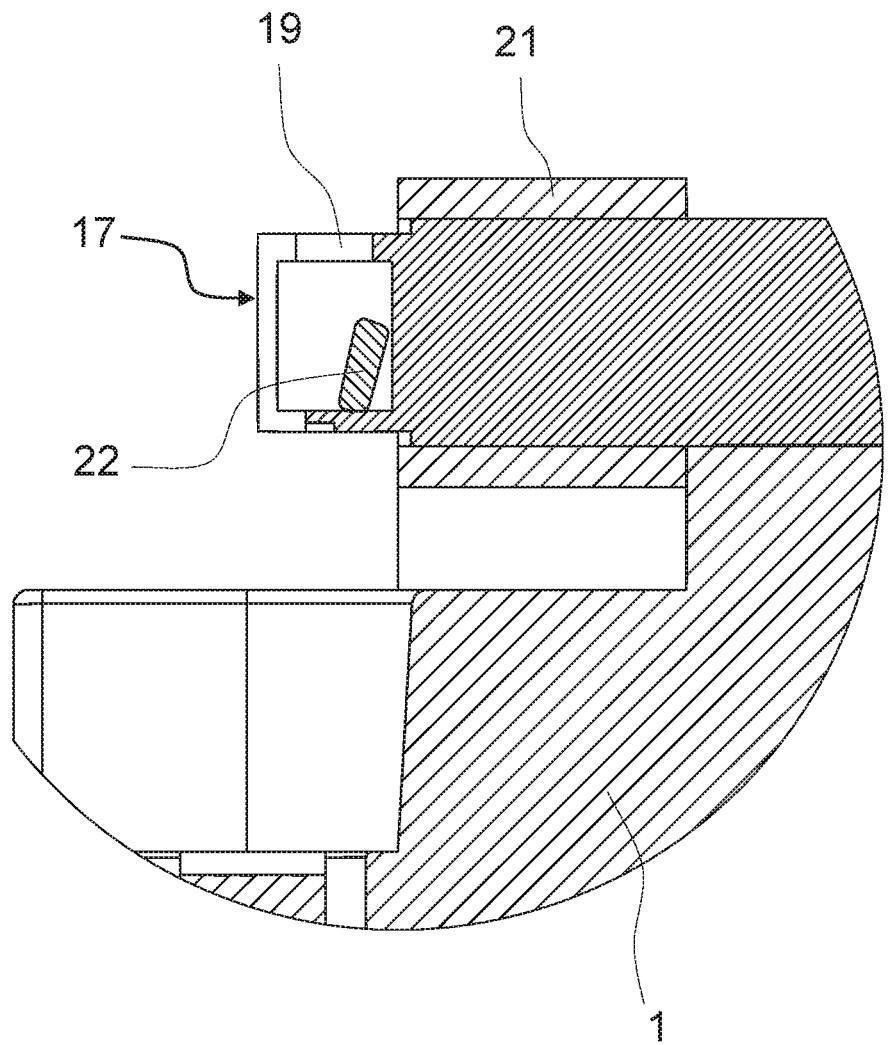

The ear tag parts 6 and 10 are now removed from the applicator pliers, namely to the left according to FIG. 1F. In doing so, however, the removal head 17 remains in its guide 21 in the applicator pliers 1. The mandrel shaft 9 is withdrawn sideways from the removal chamber 18. For this purpose, in its left side wall in the figure it has a slot 23 which opens when the mandrel shaft 9 is withdrawn sideways, allows the mandrel shaft through and then closes again as shown in FIG. 1G. The material of the removal head 17 must have suitable elasticity for this purpose.

The removal head 17 can now be removed from the applicator pliers 1 from the position shown in FIG. 1G and sent, for example, to a laboratory where the required analyses can be carried out. For this purpose, the sample 22 is preferably placed in a transport container and sealed airtight.

If the movement sequence as shown in FIGS. 1B to 1G is again compared, then it can be seen that the mandrel 8 is moved on a linear first movement path, which, in the figures, runs from top to bottom, from the position according to FIG. 1B to the position according to FIG. 1F. When it is still in the ear, the sample 22 severed from the ear 16 initially lies exactly in the path of the mandrel 8 and, as FIG. 1O shows, is initially transported in the movement path of the mandrel 8 as far as the removal opening 19. However, on further movement of the mandrel 8, as FIG. 1D shows, the sample 22 is no longer transported in the movement path of the mandrel 8 but, as in particular FIG. 1E shows, remains held in the removal chamber 18. The mandrel 8 continues downwards and, in doing so, moves the sample 22 to the side, namely to the right according to the figures. As FIG. 1E shows compared with FIG. 1D, the whole removal head 17 is also moved somewhat to the side at the same time. This therefore results in a sideways movement of the sample 22 on a section of the path after the process of severing the sample 22.

In particular, this prevents the sample being transported by the mandrel 8 into the chamber 13 below the hole 12 where it would be difficult to access.

FIGS. 2A to 2F show a second embodiment of the invention in which, apart from a few exceptions, the components correspond to those of the embodiment previously described. The same references are used wherever possible.

FIG. 2A shows a position corresponding to FIG. 1B. The mandrel 8 sits with the mandrel shaft 9 on the mandrel pin 5 and is now to be moved through the ear 16 and the removal head 17 and through the hole 12 into the chamber 13.

In the first embodiment, as can be seen, for example, in FIGS. 1C and 1D, the removal opening 19 of the removal chamber 18 has a sharp edge which, together with the conical angled surface of the mandrel 8, exerts a cutting effect on the sample 22 which is to be cut from the ear 16. In the first embodiment shown, the sample 22 is therefore at least predominantly severed with a cutting action.

In the second embodiment of FIGS. 2A to 2F, the action is to be less cutting-off, and rather tearing-off. For this purpose, as FIG. 2A shows, the opening 19 of the removal chamber 18 is provided with a funnel-shaped collar 24, which FIG. 2B shows in plan view. At three points on its circumference (see FIG. 2B), the collar 24 is provided with a radially-arranged row of needles 25. These needles 25 can be seen most clearly in FIG. 2F. They each have a barbed hook at their free end and with this penetrate the tissue of the ear 16 when, as FIG. 2C shows for example, it is pressed against the collar 24.

If the mandrel is pressed down further, then, as FIG. 2D shows, the collar 24, which sits elastically in the removal opening 19, is pressed downwards out of said opening and, in doing so, the sample 22 held by its needles 25 is finally torn from the ear 16, which remains outside the removal opening 19. On further downwards movement of the mandrel 8 according to FIG. 2E, the collar 24 with the sample 22 is moved sideways by the mandrel 8 and deposited in the removal chamber 18. FIG. 2F shows a position of the mandrel 8 at the very bottom. This has now also moved the removal head 17 in its guide 21 to the side. In doing so, the mandrel shaft 9 has emerged sideways through the slot 23. The sample can now be removed from the applicator pliers together with the removal head 17.

If the first embodiment of FIGS. 1A to 1G is compared with the second embodiment of FIGS. 2A to 2F, then it can be seen that the essential difference consists in how the sample 22 is severed from the ear 16, namely in one case substantially by cutting and in the other case substantially by tearing. If necessary, these two options can also be combined with one another.

Common to both embodiments is the severing of the sample 22 from the ear 16 by a collision of the mandrel 8 with the removal opening 19 of the removal head 17. This occurs after the mandrel 8 has passed through the ear 16. For this purpose, the removal head 17 is arranged on the side of the ear 16 facing the hole 12 in the vicinity of the hole 12. By itself, the sample 22 would lie in the path of the mandrel 8 and would be transported thereby through the hole 12 into the chamber 13. According to the invention, however, a sidewards component of the movement is imparted to the sample 22 due to interaction between the mandrel 8 and the removal head 17, so that ultimately the sample 22 lands in the removal chamber 18 in the removal head 17 and only the mandrel 8 in the chamber 13.

In the embodiments previously discussed, the sample 22 is substantially severed by interaction of the mandrel 8 with the removal opening 19. If, in doing so, the concentric geometry of the arrangement of the mandrel relative to the removal opening 19 is taken into account, then a sample could be produced which encompasses the mandrel in the form of a ring. This could result in the unfavorable tendency for the mandrel 8 to transport the sample into the chamber 13. Devices, which are not shown and which cut this ring on further penetration of the mandrel so that it is reliably separated from the mandrel, are therefore advantageous.

In addition, the sample may initially to all intents and purposes be only partially severed and remain connected to the ear by means of a thin strand of tissue for a period of time, e.g. until the end of the transverse movement. The strand of tissue can be used, for example, to pull a ring-shaped sample sitting on the mandrel from said mandrel. Ultimately, the strand of tissue can be finally severed. In doing so, the initially only partial severing operation can be carried out with a first severing device, and a second severing device can be provided for the final severing operation.

FIGS. 3A to 3D show a third embodiment of the invention which differs somewhat further from the previous embodiments. However, most parts remain unchanged and are provided with the same references.

As FIG. 3A shows, as an alternative to the previous embodiments, the removal head 17 is arranged directly in the axis of the mandrel 8 in front thereof in its direction of movement, and in addition is retained on the conical outer surface of the mandrel 8 in an interlocking manner by means of a funnel-shaped guide. In turn, the removal head 17 has the removal chamber 18 and the removal opening 19, which is open in the direction of movement of the mandrel 8 and forms a ring cutter.

On penetrating the ear, as FIG. 3B shows, the sample 22 is cut off by the ring cutter and retained in the removal chamber 18 of the removal head 17.

The conventional arrangement, as shown in the publication cited in the introduction as generic, for example, can be seen here.

Unlike this, however, the removal head 17 is not conveyed into the chamber 13 but, as FIG. 3B shows, enters the opening of a container 26, which is held upright at an angle above the hole 12, before reaching the hole 12. As FIG. 3C shows, on further downwards movement of the mandrel 8, the removal head 17, which runs against the wall of the container 26, tilts at an angle and is pushed into the container by the mandrel 8 which continues to run downwards. Finally, on further downwards movement, the container 26 is also pushed to the side until it comes up against a stop on an angled guide 27, which is shown in FIG. 3C, as is shown in FIG. 3D. From there, the container, which, with appropriate design of the removal head 17, can be sealed airtight thereby, can be removed. It can be used as a transport container to the laboratory.

Here too, the sample 22 is moved sideways relative to the movement path of the mandrel 8 after it has been severed from the ear. However, in this embodiment of FIG. 3A to 3D, the sample 22 is moved together with the removal head 17.

In the first three embodiments of the invention previously discussed, only the mandrel 8 is driven. The severing action is generated therefrom in conjunction with the removal head 17, and the severed sample 22 is then moved to the side.

FIGS. 4A to 4C show a fourth embodiment of the invention with somewhat different kinematics. Again, the previous references are used wherever possible.

Once again, the applicator pliers 1 guide the bolt 4 to drive the mandrel 8. A second bolt 28, which is coupled to a kinematic connection (not shown) to the drive of the bolt 4, is mounted on the applicator pliers 1 at an angle to the bolt 4. The second bolt 28 holds a tube 29, at the end of which is fixed the removal head 17, which, in accordance with the design of the third embodiment, has a tube cutter on its face side.

If the movements of the removal head 17 are compared, then it can be seen that, on downward movement of the bolt 28, the removal head 17 first penetrates the ear 16 with its face-side ring cutter and is then inserted in the container 26 which is retained in the foot part of the applicator pliers 1. The removal head 17 can securely seal the container, after which the sample 22 stored in the removal head 17 is sealed airtight in the interior of the container 26.

The bolt 28 can then be pulled back up, as FIG. 4C shows.

In this embodiment of the applicator pliers, the mandrel 8 is driven separately from the removal head 17 but the movement thereof is coupled thereto via a kinematic arrangement. In FIG. 4A, the mandrel 8 is not yet engaged. However, it is to pass through the ear 16, namely at the same point at which a hole has previously been cut by the ring cutter of the removal head 17. In its movement, the mandrel 8 must therefore lag somewhat behind the movement of the removal head 17, so that the removal head 17 has passed completely through the hole in the ear 16 before the mandrel 8 arrives. This instant is shown in FIG. 4B. The removal head 17 is already beneath the ear so that the mandrel 8 can now pass through the hole in the ear 16. In doing so, in the embodiment shown, it penetrates the tube 29, as FIG. 4B shows. FIG. 4C shows the mandrel shortly before reaching its final position in the hole part 10 of the ear tag.

As can be seen from this fourth embodiment, here too the severed sample 22 undergoes a movement component which is oriented to the side relative to the movement path of the mandrel 8.

| List of references | |
|---|---|
| 1 | Applicator pliers |
| 2 | Axis hole |
| 3 | Guide hole |
| 4 | Bolt |
| 5 | Mandrel pin |
| 6 | Mandrel part |
| 7 | Mandrel plate |
| 8 | Mandrel |
| 9 | Mandrel shaft |
| 10 | Hole part |
| 11 | Hole plate |
| 12 | Hole |
| 13 | Chamber |
| 14 | Housing |
| 15 | Edge |
| 16 | Ear |
| 17 | Removal head |
| 18 | Removal chamber |
| 19 | Removal opening |
| 20 | Plunger |
| 21 | Guide |
| 22 | Sample |
| 23 | Slot |
| 24 | Collar |
| 25 | Needle |
| 26 | Container |
| 27 | Angled guide |
| 28 | Second bolt |
| 29 | Tube |

What is claimed:

1. A method for attaching an ear tag to an ear and for severing a sample containing tissue of the ear from the ear, the method comprising:

moving a mandrel, which is fixed to a mandrel part of the ear tag, by means of applicator pliers along a first movement path through the ear and into a hole formed in a hole part of the ear tag and such that the mandrel becomes anchored in the hole formed in the hole part of the ear tag, and obtaining the sample with the aid of a removal head that is removably mounted on the applicator pliers, wherein the sample moved transversely with respect to the first movement path of the mandrel and thereby prevented from engaging with the hole formed in the hole part of the ear tag before the mandrel becomes anchored in the hole.

2. The method of claim 1, further comprising:

after penetrating the ear with the mandrel, pressing part of the ear with the mandrel against a removal opening in the removal head thereby severing the sample from the ear.

3. The method of claim 2, wherein the severing occurs by cutting.

4. The method of claim 2, wherein the severing occurs by tearing.

5. The method of claim 1, further comprising pushing the removal head through the ear with the mandrel as the mandrel moves along the first movement path toward the hole formed in the hole part of the ear tag to sever the sample from the ear and retain the sample in the removal head, and then pushing the removal head with the mandrel against a device that deflects the removal head and the sample retained therein transversely with respect to the first movement path of the mandrel as the mandrel continues to move along the first movement path toward the hole formed in the hole part of the ear tag.

6. The method of claim 1, further comprising moving the removal head separately from the mandrel on a path which is at an angle to the first movement path and cutting the ear by penetrating the ear with the removal head.

7. A device for attaching an ear tag to an ear and for severing a sample containing tissue of the ear from the ear, the device comprising:

applicator pliers;

the ear tag; and a removal head for retaining the sample;

wherein the removal head is removably mounted on the applicator pliers, wherein a mandrel is fixed to a mandrel part of the ear tag, wherein the mandrel is configured to be brought by means of the applicator pliers on a first movement path running through the ear and into a hole formed in a hole part of the ear tag and to become anchored in the hole formed in the hole part of the ear tag, and wherein the removal head is configured such that the sample retained therein moves transversely with respect to the first movement path of the mandrel and is thereby prevented from engaging with the hole formed in the hole part of the ear tag before the mandrel becomes anchored in the hole.

8. The device of claim 7, wherein the device is configured to sever the sample from the ear by pressing part of the ear with the mandrel against a removal opening in the removal head or by pushing the removal head through the ear.

9. The device of claim 8, wherein the device is configured such that traverse movement of the sample with respect to the first movement path of the mandrel is produced by interaction between the mandrel and the removal head.

10. The device of claim 8, wherein the device is configured such that the removal head is removably mounted on the applicator pliers such that it does not move during ear tag attachment and movement of the mandrel along the first movement path presses the part of the ear against the removal opening in the removal head to sever the sample form the ear.

11. The device of claim 8, further comprising a container to accommodate the sample.

12. The device of claim 8, wherein the removal head functions as a container for the sample.

13. The device of claim 12, wherein the removal opening of the removal head functions as a cutter for severing the sample from the ear when contacted by the mandrel.

14. The device of claim 12, wherein the removal head has a needle arrangement whichis contactable by the mandrel.

15. The device of claim 12, wherein the removal head has a slot oriented parallel to the movement path of the mandrel.

16. The device of claim 8, wherein the mandrel has a surface for penetrating the ear which runs at an angle to the first movement path of the mandrel.

17. The device of claim 16, wherein the surface is a conical surface.

18. The device of claim 7, wherein the removal head is configured to be arranged on the mandrel before the mandrel is moved along the first movement path, and wherein the device further comprises an angled guide for deflecting the removal head retaining the sample transversely with respect to the first movement path of the mandrel before the mandrel becomes anchored in the hole.

19. The device of claim 7, wherein the device is configured to guide the removal head on a second movement path, which is arranged at an angle to the first movement path so as to bisect the first movement path at a point of penetration of the ear, and wherein the device is configured such that the removal head is guided so as to reach the point of penetration at a time before the mandrel penetrates the ear.

* * * * *

UNITED STATES PATENT AND TRADEMARK OFFICE
CERTIFICATE OF CORRECTION

Page 1 of 1

PATENT NO. : 11,109,568 B2
APPLICATION NO. : 16/193915
DATED : September 7, 2021
INVENTOR(S) : Alexander Berner It is certified that error appears in the above-identified patent and that said Letters Patent is hereby corrected as shown below:

In the Claims

In Column 9, Line 3, in Claim 10, Change "form" to --from--

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*